(12) United States Patent
Ziemer

(10) Patent No.: US 7,150,754 B2
(45) Date of Patent: Dec. 19, 2006

(54) SCALPEL BLADE HOLDER AND SCALPEL

(75) Inventor: Frank Ziemer, Brügg b. Biel (CH)

(73) Assignee: SIS AG Surgical Instrument Systems, Brugg b. Biel (CH)

( * ) Notice: Subject to any disclaimer, the term of this patent is extended or adjusted under 35 U.S.C. 154(b) by 529 days.

(21) Appl. No.: 10/648,274

(22) Filed: Aug. 27, 2003

(65) Prior Publication Data
US 2005/0101978 A1    May 12, 2005

(30) Foreign Application Priority Data
Aug. 30, 2002    (EP) .................. 02405757

(51) Int. Cl.
*A61B 17/32*    (2006.01)
(52) U.S. Cl. ..................... 606/167
(58) Field of Classification Search ......... 606/160, 606/161, 166, 167, 170, 184, 187, 190, 210
See application file for complete search history.

(56) References Cited

U.S. PATENT DOCUMENTS

| 136,595 | A | * | 3/1873 | Pleasants | ............... 100/59 |
| 878,004 | A | * | 2/1908 | Jahn | ............... 15/443 |
| 3,384,386 | A | | 5/1968 | Ward | |
| 4,149,811 | A | | 4/1979 | Coffman | |
| 5,897,574 | A | * | 4/1999 | Bonutti | ............... 606/232 |
| 6,039,053 | A | | 3/2000 | Turrentine | |

FOREIGN PATENT DOCUMENTS

| FR | 483.593 A | 7/1917 |
| WO | WO 02/49520 A1 | 6/2002 |

* cited by examiner

*Primary Examiner*—Kevin T. Truong
(74) *Attorney, Agent, or Firm*—Oliff & Berridge PLC

(57) ABSTRACT

Proposed are a scalpel blade holder and a scalpel with a scalpel blade holder, which make it possible for a user to determine the rotation of the scalpel about the center axis of the scalpel blade holder without eye contact with the scalpel or with the scalpel blade. The handle region of the scalpel blade holder comprises three lateral faces which are disposed such that a cross-section with a substantially triangular envelope results for the handle region. The envelope of the cross-section of the handle region has substantially the form of an arc triangle whose corners are rounded. A plurality of tactile identifying features are designed as protrusions in the form of ribs extending over two of the lateral faces and running crosswise to the longitudinal axis of the scalpel blade holder. One of the tactile identifying features is designed as a recess, and is disposed on the remaining third lateral face, and extends over part of the length of the scalpel blade holder. By means of his sense of touch, the user can determine the alignment of the scalpel blade with regard to its rotation about the center axis of the scalpel blade holder.

13 Claims, 3 Drawing Sheets

SCALPEL BLADE HOLDER AND SCALPEL

TECHNICAL FIELD

The present invention relates to a scalpel blade holder and a scalpel. The invention relates in particular to a scalpel blade holder and a scalpel having a handle region and means of attaching a scalpel blade.

BACKGROUND ART

Conventional scalpel blade holders and scalpels have means for detachable or non-detachable fixing of scalpel blades and have a handle region which makes it possible for the user to hold the scalpel, or respectively the scalpel blade holder, with the fingers of one hand. When using scalpels and scalpel blade holders, the user must make sure by means of a glance that he has the instrument in his fingers in such a way that the scalpel blade is correctly aligned and the cutting edge of the scalpel blade faces in the desired direction. To align the scalpel blade, the user must therefore glance away from the place where the operative procedure is supposed to be carried out, which is inconvenient, especially when microscopes or magnifying glasses are being used, and which leads to unnecessary time delays and losses of concentration.

DISCLOSURE OF INVENTION

It is an object of the present invention to propose a new scalpel and a new scalpel blade holder which do not have the drawbacks of the state of the art and which make it possible in particular to align a scalpel blade without eye contact.

The above-mentioned objects are achieved through the present invention in particular in that the handle region of the scalpel blade holder comprises three lateral faces which are disposed such that a cross-section with a substantially triangular envelope results for the handle region, and at least one of the lateral faces is provided with tactile identifying features. The triangular envelope of the cross-section of the handle region facilitates a proper holding of the scalpel blade holder between middle finger, thumb and index finger, the scalpel blade holder and thus the scalpel fixed thereto being able to assume only three different rotational states about the center axis of the handle region of the scalpel blade holder, with respect to the fingers. Since at least one of the three lateral faces of the handle region is provided with tactile identifying features, the user can thus determine the alignment of the scalpel blade holder and of the scalpel fixed thereto via his fingers by means of his sense of touch, without having to make eye contact with the scalpel or with the scalpel blade holder for this purpose. In other words, without looking at the scalpel blade holder or at the scalpel blade, the user can identify, via his sense of touch, the alignment of the scalpel blade with a view to its rotation about the center axis of the handle region of the scalpel blade holder. The triangular envelope of the cross-section of the handle region has moreover the advantage that the scalpel blade holder in laid down state does not roll away and the scalpel fixed thereto does not become damaged.

In a preferred embodiment variant, the envelope of the cross-section of the handle region has substantially the form of an arc triangle and the corners of the envelope of the cross-section of the handle region are rounded. The arctriangular shape makes possible a better grip between middle finger, thumb and index finger. The rounded corners also contribute to a better grip, and in addition prevent the user from hurting himself on the corners or damaging protective gloves.

Preferably, at least one of the tactile identifying features is designed as protrusion. Protrusions in particular can be easily perceived by sense of touch of the fingers and do not need to be dimensioned as big as tactile identifying features designed as recesses. Above and beyond this, the tactile identifying features can be designed such that they represent an identification code, for instance in a way resembling braille, identifying the type of scalpel fixed on the scalpel blade holder.

In a preferred embodiment variant, at least one of the tactile identifying features is designed as recess. Especially when the recess is dimensioned large, for example when it extends over at least part of the length of the scalpel blade holder, it can serve to save manufacturing material and reduce the overall weight of the scalpel blade holder. Recesses of large dimension can be taken into consideration moreover in the design and dimensioning of wall thicknesses.

In a preferred embodiment variant, at least two of the three lateral faces of the handle region are each provided with tactile identifying features differing from one another. For example, at least one of the tactile identifying features is designed as protrusion and extends over two lateral faces of the handle region, and at least one of the tactile identifying features is designed as recess and is disposed on the remaining third lateral face of the handle region. Such a configuration with differing tactile identifying features further facilitates, by means of the sense of touch of the fingers, the positioning and alignment of the scalpel blade holder and of the scalpel fixed thereto. That lateral face of the handle region which is supposed to be supported on the middle finger can be provided with an identifying feature designed as a recess while the two other lateral faces of the handle region, held by the thumb and the index finger, are provided with tactile identifying features designed as protrusions.

In a preferred embodiment variant, the protrusions are designed as ribs extending crosswise to the longitudinal axis of the scalpel blade holder. This has the additional advantage that the ribs offer a better hold in the direction of the longitudinal axis of the scalpel blade holder and prevent a sliding of the fingers in this direction, especially when the fingers are wet or are covered with a wet glove.

In an embodiment variant, the scalpel blade holder has an end region which tapers from the handle region, and the means of fixing a scalpel blade comprise a bore, running axially through the end region, for receiving the scalpel blade.

In an embodiment variant, the bore axis runs offset from the center axis of the handle region and parallel to the center axis of the handle region. By means of the parallel offsetting of the bore axis, the scalpel fixed on the scalpel blade holder can be offset more closely to the lateral face which is supported on the middle finger, which brings the scalpel blade closer to the object to be treated. The smaller distance of the scalpel blade to the object of treatment decreases the distances of movement and improves the working precision, in particular during use in ophthalmology.

The present invention also relates to a scalpel comprising an above-described scalpel blade holder and a scalpel blade fixed thereto.

BRIEF DESCRIPTION OF DRAWINGS

An embodiment of the present invention will be described in the following with reference to an example. The example of the embodiment is illustrated by the following attached figures.

MODE(S) FOR CARRYING OUT THE INVENTION

Figure 1:
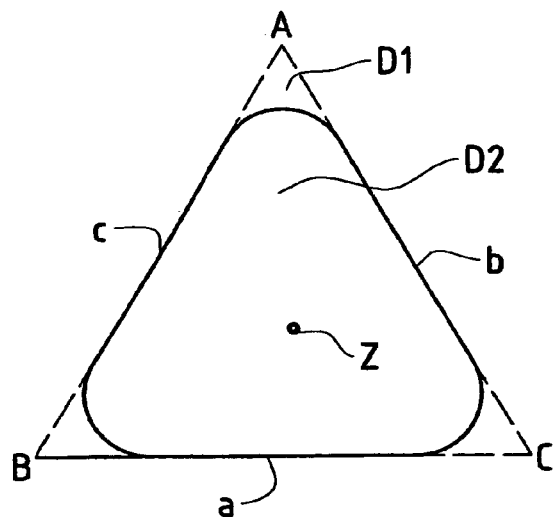
FIG. 1 shows a sectional view of a scalpel blade holder illustrating a cross-section of the handle region in the form of a triangle with rounded corners.

In FIGS. 1 to 7 same components corresponding to one another are designated by the same reference numerals.

Figure 4:
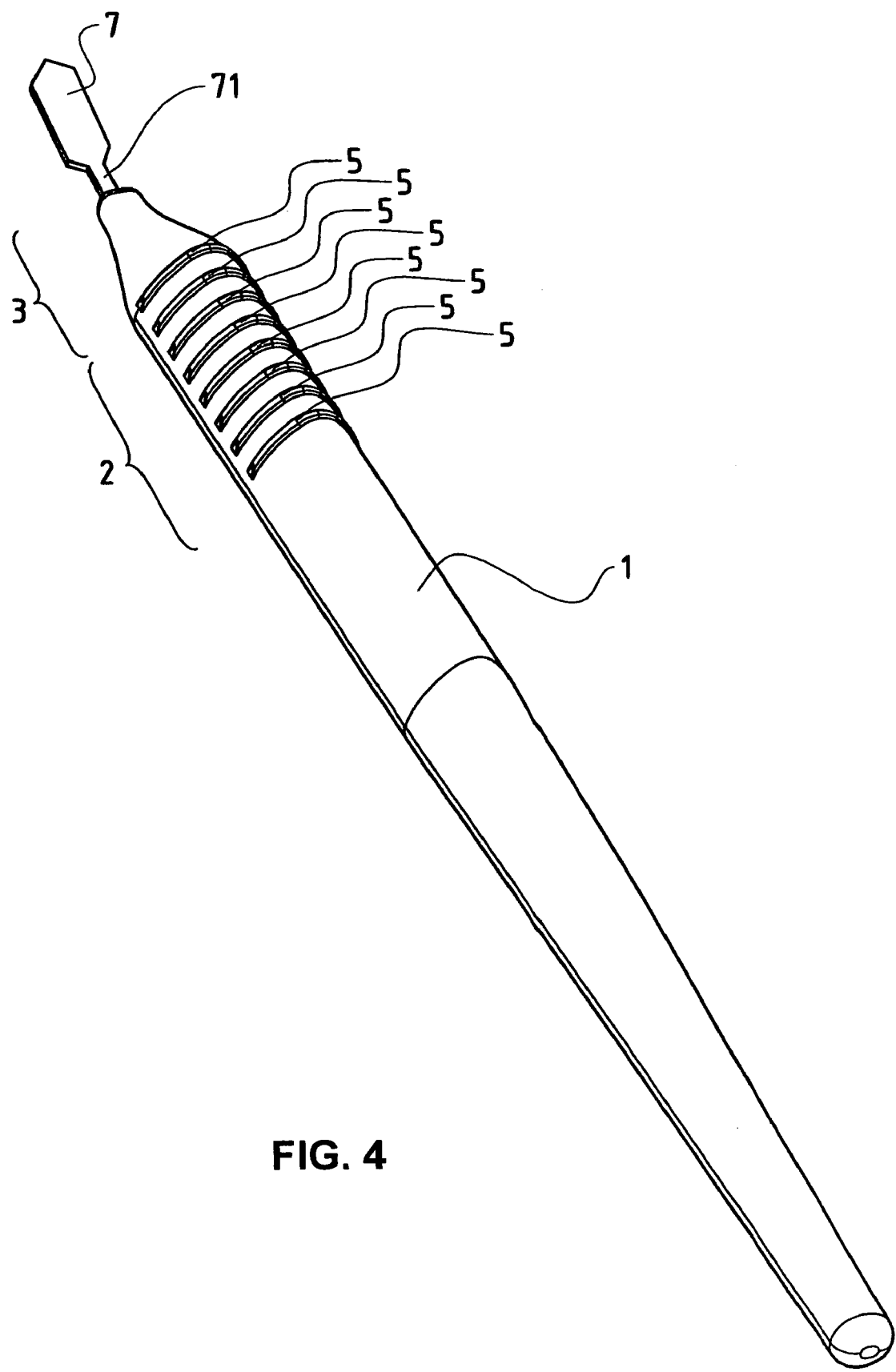
FIG. 4 shows a three-dimensional view of the scalpel with a scalpel blade holder and a scalpel blade fixed thereon.

Shown in FIG. 4 is a three-dimensional view of a scalpel with a scalpel blade holder 1 and a scalpel blade 7 fixed thereon. The scalpel blade holder 1 has a handle region 2 and an end region 3 tapering from the handle region 2. The handle region 2 has tactile identifying features in the form of protrusions 5.

Figure 5:
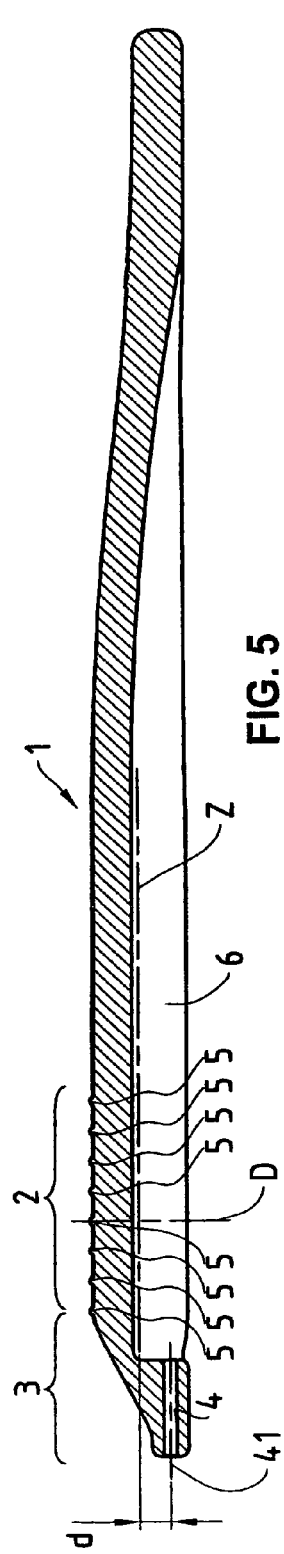
FIG. 5 shows a longitudinal section of the scalpel blade holder with protrusions in the handle region and a recess over part of the length of the scalpel blade holder.

As shown in FIG. 5, the end region 3 has a bore 4, in which the attachment cylinder 71 of the scalpel blade 7 (see FIG. 4) is insertable for attaching the scalpel blade 7. To attach the scalpel blade 7, the attachment cylinder 71 is glued, bonded or welded in the bore 4. The attachment can also take place by means of press fit. The scalpel blade holder 1 can also be molded around the attachment 71 in an injection molding process; in so doing the attachment cylinder 71 preferably has structural elements on its surface.

Figure 2:
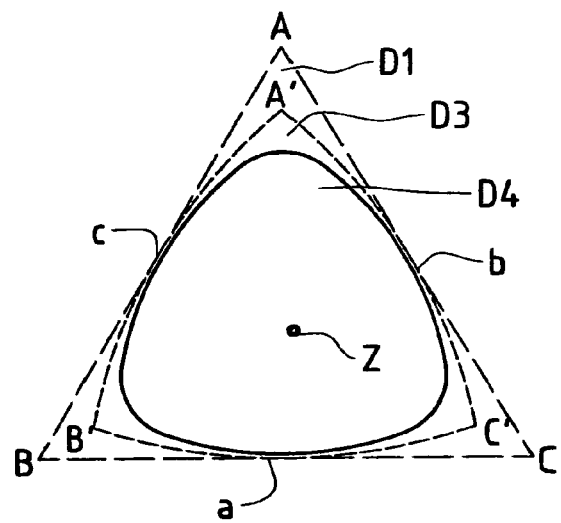
FIG. 2 shows a sectional view of the scalpel blade holder illustrating a cross-section of the handle region in the form of an arc triangle with rounded corners.
Figure 3:
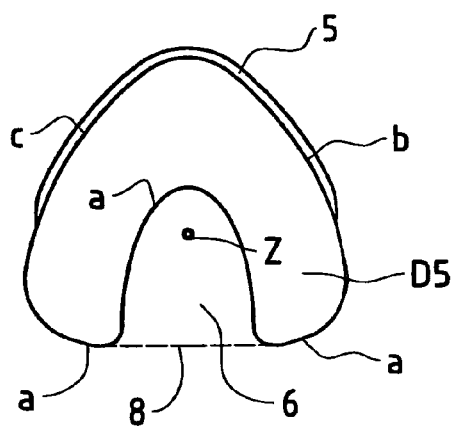
FIG. 3 shows a sectional view of the scalpel blade holder illustrating a cross-section of the handle region having an envelope in the form of an arc triangle, with rounded corners, provided with a protrusion and a recess.

Shown in FIGS. 1, 2 and 3 are sectional views of the scalpel blade holder 1 illustrating different possible cross-sectional shapes D1, D2, D3, D4, D5 for the handle region 2, which all have a substantially triangular envelope. In FIGS. 1, 2 and 3 the reference symbols a, b and c designate in each case the lateral faces of the handle region 2. The triangle shown in FIGS. 1 and 2 with the corners A, B and C corresponds to an equilateral, triangular cross-section D1. Compared to the cross-section D1, the cross-section D2 has rounded corners A, B and C. The envelope of the cross-section D3 corresponds to an arc triangle resulting from circular arcs intersecting at the points of intersection A', B', C'. Compared to the cross-section D3, the corners formed by the points of intersection A', B' and C' are rounded in the cross-section D4. One skilled in the art will understand that the arc triangle can also be designed using arcuate shapes shapes other than circular arcs. Moreover the arcs can be disposed such that a cross-sectional shape results with con-cave sides. Above and beyond this, the cross-sectional shape of the handle region 2 does not necessarily have to be symmetrical to the center axis Z, i.e. the triangular envelope does not necessarily have to be designed to be equilateral and the different corners do not have to be all designed the same. Starting with the triangle with the corners A, B and C, for instance just one corner A can be rounded or oblated, so that the substantially triangular envelope encloses a trapezoidal cross-section, or two corners B, C can be very rounded whereas the third corner A has no rounding, so that the substantially triangular envelope encloses a drop-shaped cross-section.

Figure 6:
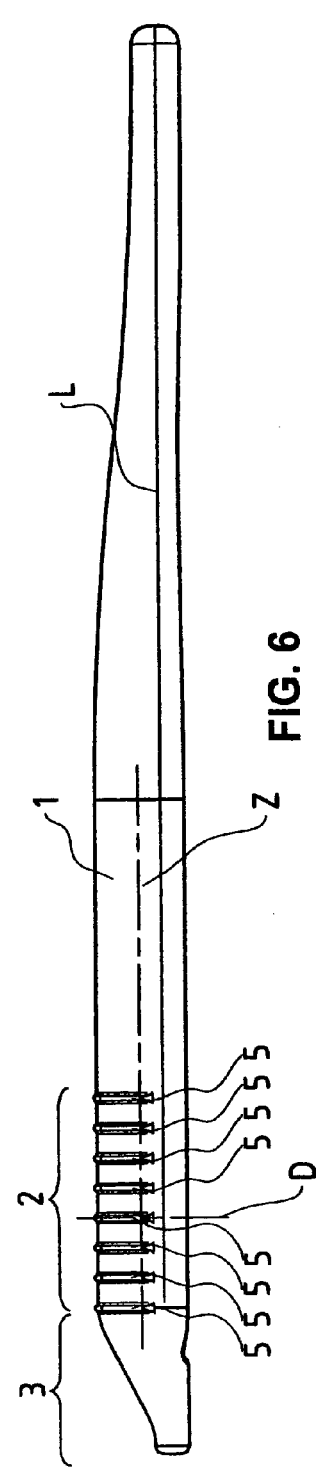
FIG. 6 shows a side view of the scalpel blade holder with protrusions in the handle region.
Figure 7:
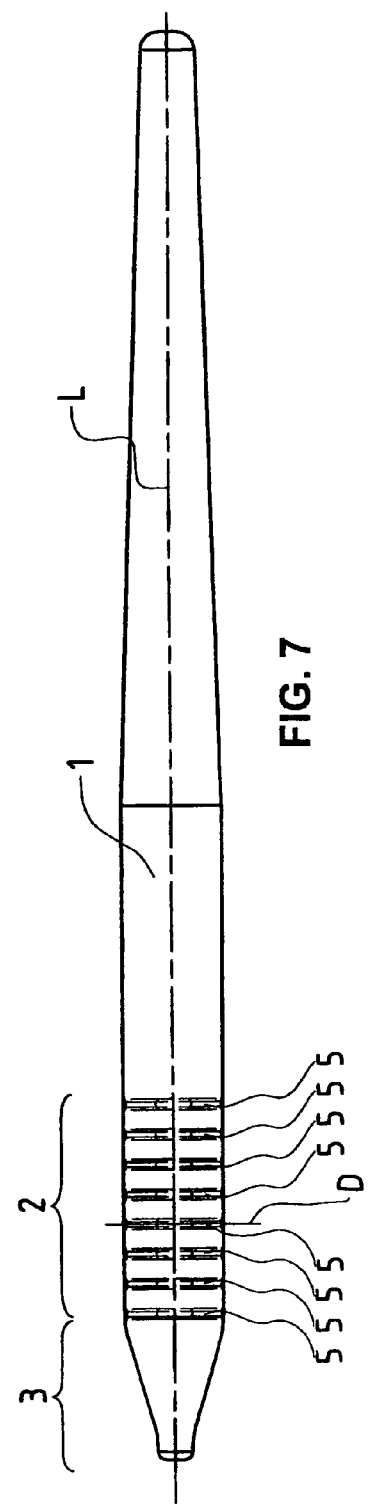
FIG. 7 shows a top view of the scalpel blade holder with protrusions in the handle region.

The view shown in FIG. 3 of a cross-section of the handle region 2 corresponds to the cross-section D marked in FIGS. 5, 6 and 7. In this preferred embodiment of the scalpel blade holder 1, cross-section D5 of the handle region 2 has a substantially triangular envelope 8 having the shape of an arc triangle with rounded corners, which corresponds to the cross-sectional shape D4 shown in FIG. 2. As shown in FIG. 3, the cross-section D5 has a recess 6 resulting from an indentation of the lateral face a.

As shown in FIG. 5, the recess 6 is designed as a cut out. It extends over the entire handle region 2, and stretches over the greater part of the scalpel blade holder. As can be seen from FIGS. 3 and 5, the recess 6 is designed such that a substantially equal wall strength results in the entire scalpel blade holder 1, which is especially advantageous in the manufacture of the scalpel blade holder 1 by an injection molding process (for example out of plastic or light metal such as aluminum). One skilled in the art will understand that the recesses 6 can also be designed having other shapes and in particular smaller, for instance as circular hollows or other geometric forms.

It can seen furthermore in FIG. 3 that a protrusion 5 is provided on the cross-section D5 extending in each case over part of the lateral faces b and c. As shown in FIGS. 4, 5, 6 and 7, a plurality of such protrusions 5 are disposed in the handle region 2. The protrusions 5 are designed in the form of ribs running crosswise to the longitudinal axis L of the scalpel blade holder 1. One skilled in the art will understand that the protrusions 5 can also be designed in another form, for instance as raised dots such as in braille or in other geometric shapes.

The protrusions 5 und/or the recesses 6 can also be designed and/or disposed such that they represent a code conveying information to the user, via the sense of touch, about the scalpel he is using, for instance about the type of scalpel blade 7.

As shown in FIG. 5, the bore axis 41 is offset from the center axis Z of the handle region 2 by the distance d.

Finally it should be stated here that further embodiments of the scalpel blade holder 1 follow from the foregoing for one skilled in the art and are within the scope of the invention. For example, the lateral faces a, b, c of the handle region 2 can be provided with different side-specific tactile features varying in their geometric design and/or configuration. Furthermore, for the sake of clarity, it should be added that instead of a scalpel blade 7 with a cutting surface other instruments can also be fixed to the scalpel blade holder 1 which do not necessarily need to have a cutting surface.

List of Reference Symbols

| | |
|---|---|
| 1 | scalpel blade holder |
| 2 | handle region |
| 3 | end region |
| 4 | bore |

-continued

| 5 | protrusion |
| 6 | recess |
| 7 | scalpel blade |
| 8 | envelope |
| 41 | bore axis |
| 71 | attachment cylinder |
| A, B, C | corners |
| A', B', C' | points of intersection |
| a, b, c | lateral faces |
| d | distance |
| D | cross-section |
| D1 | triangular cross-section |
| D2 | triangular cross-section with rounded corners |
| D3 | cross-section in the form of an arc triangle |
| D4 | cross-section in the form of an arc triangle with rounded corners |
| D5 | cross-section with envelope in the form of an arc triangle with rounded corners |
| L | longitudinal axis |
| Z | center axis |

The invention claimed is:

1. A scalpel, comprising:
a scalpel blade holder with a handle region, and
a scalpel blade attached to the scalpel blade holder, wherein
the handle region comprises three lateral faces which are disposed such that a cross-section with a substantially triangular envelope results for the handle region, and
at least one of the lateral faces is provided with tactile identifying features, the tactile identification features enabling the user to determine, using the sense of touch in his fingers, the orientation of a scalpel blade attached to the blade holder in relation to its rotation about a center axis of the handle region.

2. Scalpel according to claim 1, wherein at least one of the tactile identifying features is designed as a protrusion.

3. Scalpel according to claim 1, wherein at least one of the tactile identifying features is designed as a recess.

4. Scalpel according to claim 1, wherein the recess extends over at least part of the length of the scalpel blade holder.

5. Scalpel according to claim 1, wherein at least two of the lateral faces are each provided with tactile identifying features different from one another.

6. Scalpel according to claim 1, wherein at least one of the tactile identifying features is designed as a protrusion and extends over two of the lateral faces, and at least one of the tactile identifying features is designed as a recess and is disposed on the remaining third lateral face.

7. Scalpel according to claim 1, wherein the protrusions are designed as ribs which extend crosswise to the longitudinal axis of the scalpel blade holder.

8. Scalpel according to claim 1, wherein the envelope of the cross-section of the handle region has substantially the form of an arc triangle, and the envelope of the cross-section of the handle region has rounded corners.

9. Scalpel according to claim 1, wherein the scalpel blade holder has an end region which tapers from the handle region, and the means of attaching the scalpel blade comprises a bore, running axially through the end region, for receiving the scalpel blade.

10. Scalpel according to claim 1, wherein a bore axis of said bore runs offset from a center axis of the handle region and parallel to the center axis of the handle region.

11. Scalpel according to claim 1, wherein the tactile identifying features are designed such that they represent an identification code identifying a type of scalpel blade.

12. A scalpel, comprising:
a scalpel blade holder with a handle region, and
a scalpel blade attached to the scalpel blade holder, wherein
the handle region comprises three lateral faces which are disposed such that a cross section with a substantially triangular envelope results for the handle region, the three lateral faces being arranged in such a way that, when the handle region is held properly between the middle finger, thumb, and index finger of a person using the scalpel blade holder, three different rotational states about a centre axis of the handle region can be assumed relative to the fingers, and
at least one of the lateral faces is provided with tactile identification features, the tactile identification features enabling the user to determine, using the sense of touch in his fingers, the orientation of a scalpel blade attached to the blade bolder in relation to its rotation about the centre axis.

13. A scalpel, comprising:
a scalpel blade holder with a handle region, and
a scalpel blade attached to the scalpel blade holder, wherein
the handle region comprises three lateral faces which are disposed rectilinearly along a longitudinal axis of the scalpel blade holder, such that a cross section with a substantially triangular envelope results for the handle region, the three lateral faces being arranged in such a way that, when the handle region is held properly between the middle finger, thumb, and index finger of a person using the scalpel blade holder, only three different rotational states about a centre axis of the handle region can be assumed relative to the fingers, and
at least one of the lateral faces is provided with tactile identification features, the tactile identification features enabling the user to determine, using the sense of touch in his fingers, the orientation of a scalpel blade attached to the blade holder in relation to its rotation about the centre axis.

* * * * *